US012220237B2

(12) United States Patent
Cohen et al.

(10) Patent No.: US 12,220,237 B2
(45) Date of Patent: Feb. 11, 2025

(54) SYSTEM AND METHOD OF MONITORING MENTAL HEALTH CONDITIONS

(71) Applicant: Behavidence Inc., New York City, NY (US)

(72) Inventors: Roy Cohen, Dublin (IE); Girish Srinivasan, Palatine, IL (US)

(73) Assignee: Behavidence Inc., New York, NY (US)

(*) Notice: Subject to any disclaimer, the term of this patent is extended or adjusted under 35 U.S.C. 154(b) by 0 days.

(21) Appl. No.: 17/951,408

(22) Filed: Sep. 23, 2022

(65) Prior Publication Data

US 2023/0091240 A1   Mar. 23, 2023

Related U.S. Application Data

(60) Provisional application No. 63/247,492, filed on Sep. 23, 2021.

(51) Int. Cl.
*A61B 5/16* (2006.01)
*A61B 5/00* (2006.01)
(Continued)

(52) U.S. Cl.
CPC ............ *A61B 5/165* (2013.01); *G06F 18/295* (2023.01); *G16H 20/70* (2018.01)

(58) Field of Classification Search
CPC ........ G16H 20/70; G16H 10/20; G16H 40/67; G16H 50/30; G16H 50/70; G16H 50/20; A61B 5/165; A61B 5/7267; G06F 18/295
See application file for complete search history.

(56) References Cited

U.S. PATENT DOCUMENTS

| 9,420,970 B2 | 8/2016 | Dagum |
| 9,474,481 B2 | 10/2016 | Dagum |

(Continued)

FOREIGN PATENT DOCUMENTS

WO   WO-2022067182 A1 *   3/2022

OTHER PUBLICATIONS

Ribeiro Filho, José Daniel P., et al. "Towards clustering human behavioral patterns based on digital phenotyping." 2021 IEEE 34th International Symposium on Computer-Based Medical Systems (CBMS). IEEE, 2021. (Year: 2021).*

(Continued)

*Primary Examiner* — Maroun P Kanaan
(74) *Attorney, Agent, or Firm* — PEARL COHEN ZEDEK LATZER BARATZ LLP (57) ABSTRACT

Systems and methods for assessing mental health of a person, including: recording digital activity data of the user on the mobile device, wherein the digital activity data does not include personal content of the user, applying the digital activity data to a plurality of machine learning models, wherein each of the machine learning models represents a digital phenotype for a different mental health condition, determining a similarity score for each mental health condition corresponding to each of the plurality of machine learning models based on comparing an output of the respective machine learning model to a digital phenotype for the corresponding mental health condition, outputting, at a user's display, the at least one mental health similarity score, and predicting, by the processor, at least one mental health condition of the user based on the calculated similarity scores.

16 Claims, 4 Drawing Sheets

(51) Int. Cl.
  *G06F 18/20* (2023.01)
  *G16H 20/70* (2018.01)

(56) References Cited

U.S. PATENT DOCUMENTS

| | | | |
|---|---|---|---|
| 9,538,948 | B2 | 1/2017 | Dagum |
| 9,687,187 | B2 | 6/2017 | Dagum |
| 9,693,724 | B2 | 7/2017 | Dagum |
| 10,799,186 | B2 | 10/2020 | Howard |
| 2013/0297536 | A1 | 11/2013 | Almosni et al. |
| 2018/0098737 | A1* | 4/2018 | Villazón-Terrazas ......... G06N 5/022 |
| 2018/0342327 | A1 | 11/2018 | Madan et al. |
| 2019/0117143 | A1* | 4/2019 | Fedor ............... A61B 5/165 |
| 2019/0239791 | A1* | 8/2019 | Beck ............... A61B 5/163 |
| 2019/0355474 | A1 | 11/2019 | Mellem et al. |
| 2019/0385711 | A1* | 12/2019 | Shriberg ............... G16H 10/20 |
| 2021/0219892 | A1* | 7/2021 | Gossens ............... G16H 50/20 |
| 2021/0236053 | A1* | 8/2021 | Narayan ............... A61B 5/363 |
| 2021/0391086 | A1* | 12/2021 | Miskovic ............... G16H 10/20 |

OTHER PUBLICATIONS

Asare, Kennedy Opoku, et al. "Predicting Depression From Smartphone Behavioral Markers Using Machine Learning Methods, Hyperparameter Optimization, and Feature Importance Analysis: Exploratory Study." JMIR mHealth and uHealth 9.7 (2021): e26540. (Year: 2021).*

Sahandi Far, Mehran, et al. "JTrack: a digital biomarker platform for remote monitoring of daily-life behaviour in health and disease." Frontiers in Public Health 9 (2021): 763621. (Year: 2021).*

Wang, Xuancong, et al. "HOPES: an integrative digital phenotyping platform for data collection, monitoring, and machine learning." Journal of medical Internet research 23.3 (2021): e23984. (Year: 2021).*

Garcia-Ceja, Enrique, et al. "Mental health monitoring with multimodal sensing and machine learning: A survey." Pervasive and Mobile Computing 51 (2018): 1-26. (Year: 2018).*

Mohr, David C., Mi Zhang, and Stephen M. Schueller. "Personal sensing: understanding mental health using ubiquitous sensors and machine learning." Annual review of clinical psychology 13 (2017): 23-47. (Year: 2017).*

Di Matteo, Daniel, et al. "Automated screening for social anxiety, generalized anxiety, and depression from objective smartphone-collected data: cross-sectional study." Journal of Medical Internet research 23.8 (2021): e28918. (Year: 2021).*

Ghandeharioun, Asma, et al. "Objective assessment of depressive symptoms with machine learning and wearable sensors data." 2017 seventh international conference on affective computing and intelligent interaction (ACII). IEEE, 2017. (Year: 2017).*

Gideon, John, et al. "When to intervene: Detecting abnormal mood using everyday smartphone conversations." arXiv preprint arXiv: 1909.11248 (2019). (Year: 2019).*

Levine, Lionel M., et al. "Anxiety detection leveraging mobile passive sensing." Body Area Networks. Smart IoT and Big Data for Intelligent Health: 15th EAI International Conference, BODYNETS 2020, Tallinn, Estonia, Oct. 21, 2020, Proceedings 15. Springer International Publishing, 2020. (Year: 2020).*

Neves, Felipe, et al. "Heath-PRIOR: an intelligent ensemble architecture to identify risk cases in healthcare." IEEE Access 8 (2020): 217150-217168. (Year: 2020).*

International Search Report of Application No. PCT/US2022/044547 mailed on Jan. 20, 2023.

Torous J, Chan Sr, Yee-Marie Tan S, Behrens J, Mathew I, Conrad EJ, Hinton L, Yellowlees P, Keshavan M. "Patient Smartphone Ownership and Interest in Mobile Apps to Monitor Symptoms of Mental Health Conditions: A Survey in Four Geographically Distinct Psychiatric Clinics" JMIR Ment Health. Dec. 23, 2014.

Torous J, Staples P, Shanahan M, Lin C, Peck P, Keshavan M, Onnela JP. "Utilizing a Personal Smartphone Custom App to Assess the Patient Health Questionnaire-9 (PHQ-9) Depressive Symptoms in Patients With Major Depressive Disorder" JMIR Ment Health. Mar. 24, 2015.

Torous J, Kiang MV, Lorme J, Onnela JP. "New Tools for New Research in Psychiatry: A Scalable and Customizable Platform to Empower Data Driven Smartphone Research" JMIR Ment Health. May 5, 2016.

Onnela JP. "Opportunities and challenges in the collection and analysis of digital phenotyping data" Neuropsychopharmacology. Jan. 2021;46(1):45-54.

* cited by examiner

SYSTEM AND METHOD OF MONITORING MENTAL HEALTH CONDITIONS

CROSS REFERENCE TO RELATED APPLICATION

This application claims priority to and the benefit of Provisional Application No. 63/247,492, filed Sep. 23, 2021, the entire contents of which are incorporate herein by reference in their entireties.

FIELD OF THE INVENTION

The present invention relates to monitoring of digital activity data on mobile devices. More particularly, the present invention relates to systems and methods for monitoring of cognitive health (e.g., mental health conditions) based on digital activity data.

BACKGROUND

In recent years, a greater concern has been given to mental health. Currently, there is no clear behavioral and/or biological marker for most mental health conditions or disorders. Different approaches have been tried in order to monitor or detect mental health conditions.

Clinical diagnosis of mental health disorders is usually based on psychologist/psychiatrist evaluation following the DSM-5 (Diagnostic and Statistical Manual of Mental Disorders, $5^{th}$ Edition) and ICD-II (FInternational Classification of Diseases, $11^{th}$ revision) systems. Such evaluations can be erroneous due to both the subjective perspective of the patient being used as the input to the evaluation and the subject perspective of the clinician being used as the evaluation.

At best, diagnostic and/or treatment planning is based on a "peer meeting" which can provide subject input from multiple clinicians. However, this does not provide an objective mechanism for evaluating a person.

Additional difficulty with cognitive health assessments can include an inability to track the progress/differences between sessions. For example, if a patient has a session with a clinician and reports a set of symptoms, 30 days later, the patient typically can only report a general sense of what has happened over the course of the 30 days, and may only report what is currently happening. The patient may under or over report certain symptoms based on the duration and an inability for a human to accurately track themselves. In accurate reporting of symptoms can cause improper treatment and can cause a worsening, instead of an improvement of a disorder.

Therefore, it can be desirable to allow monitoring of mental health conditions based on data that is objective and passively captured.

SUMMARY

According to some embodiments, a solution is provided for monitoring of mental health conditions by monitoring a patient's digital behavior based on, for example, data that is passively captured and analyzed based machine learned algorithms and on digital phenotyping for remote mental health assessment. Digital behavior data may be collected by a dedicated program, to be sent securely to a back-end where machine learning algorithmic models autonomously selects the most relevant features for different behavioral profiles and associates them with mental health conditions. Such solution may empower specialists or caregivers or mental health professional with richer patients' profiling so as to improve the quality of diagnostic procedures, and/or ongoing monitoring, and/or therapeutic treatment for patients. For patients, such solution may serve as a mental health navigation tool.

There is thus provided, in accordance with some embodiments of the invention, a computer implemented method for assessing mental health of a person, including: recording, by a processor of a user's mobile device, digital activity data of the user on the mobile device, wherein the digital activity data does not include personal content of the user, applying, by the processor of the user's mobile device, the digital activity data to a plurality of machine learning models, wherein each of the machine learning models represents a digital phenotype for a different mental health condition, determining, by the processor of the user's mobile device, a similarity score for each mental health condition corresponding to each of the plurality of machine learning models based on comparing an output of the respective machine learning model to a digital phenotype for the corresponding mental health condition, outputting, at a user's display, the at least one mental health similarity score, and predicting, by the processor, at least one mental health condition of the user based on the calculated similarity scores.

In some embodiments, the recording is performed by an application that runs in the background of the user's mobile device. In some embodiments, a baseline state is created for the user, wherein the baseline state is determined by the at least one mental health condition for a predefined time period, and an alert is issued, if the at least one mental health condition deviates from the baseline state by a predefined threshold.

In some embodiments, the digital activity data is used to further train the plurality of machine learning models. In some embodiments, one or more behavioral profiles is determined to train the machine learning models and wherein the behavioral profiles are clustered based on digital phenotypes indicative of at least one mental health condition. In some embodiments, the received digital activity data is used to extract features associated with information selected from the group consisting of: time of usage of the mobile device, type of program running on the mobile device, and frequency of using the same program running on the mobile device.

In some embodiments, a model is applied using ML algorithms based on autonomous clustering of behavioral profiles, wherein the training is unsupervised. In some embodiments, the ML model is trained using algorithms selected from the group consisting of: Linear Regression, Random Forest, K-Nearest Neighbor, XGD-Boost, and Support Vector Machine (SVM), wherein the training is supervised given user input as pre-labelled data. In some embodiments, reinforcement learning is performed on the ML algorithm based on a feedback loop, using a Markov Decision Process.

There is thus provided, in accordance with some embodiments of the invention, a system for assessing mental health of a person, including: a server, and a processor of a user's mobile device, wherein the processor is in communication with the server, and wherein the processor is configured to: record digital activity data of the user on the mobile device, wherein the digital activity data does not include personal content of the user, and send the recorded digital activity data to the server, wherein the server is configured to: apply the digital activity data to a plurality of machine learning models, wherein each of the machine learning models represents a digital phenotype for a different mental health condition, determine a similarity score for each mental health condition corresponding to each of the plurality of machine learning models based on comparing an output of the respective machine learning model to a digital phenotype for the corresponding mental health condition, and send at least one mental health similarity score for displaying on a user's display, and predict at least one mental health condition of the user based on the calculated similarity scores.

In some embodiments, the recording is performed by an application that runs in the background of the user's mobile device. In some embodiments, the server is configured to: create a baseline state for the user, wherein the baseline state is determined by the at least one mental health condition for a predefined time period, and issue an alert, if the at least one mental health condition deviates from the baseline state by a predefined threshold. In some embodiments, the digital activity data is used to further train the plurality of machine learning models.

In some embodiments, the received digital activity data is used to extract features associated with information selected from the group consisting of: time of usage of the mobile device, type of program running on the mobile device, and frequency of using the same program running on the mobile device. In some embodiments, the server is configured to perform ML algorithm based on autonomous clustering of behavioral profiles, wherein the algorithm is unsupervised.

In some embodiments, the ML model is trained using algorithms selected from the group consisting of: Linear Regression, Random Forest, K-Nearest Neighbor, XGDBoost, and Support Vector Machine (SVM), wherein the training is supervised given user input as pre-labelled data. In some embodiments, reinforcement learning is performed on the ML algorithm based on a feedback loop, using a Markov Decision Process.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof may occur or be performed simultaneously, at the same point in time, or concurrently.

Figure 1:
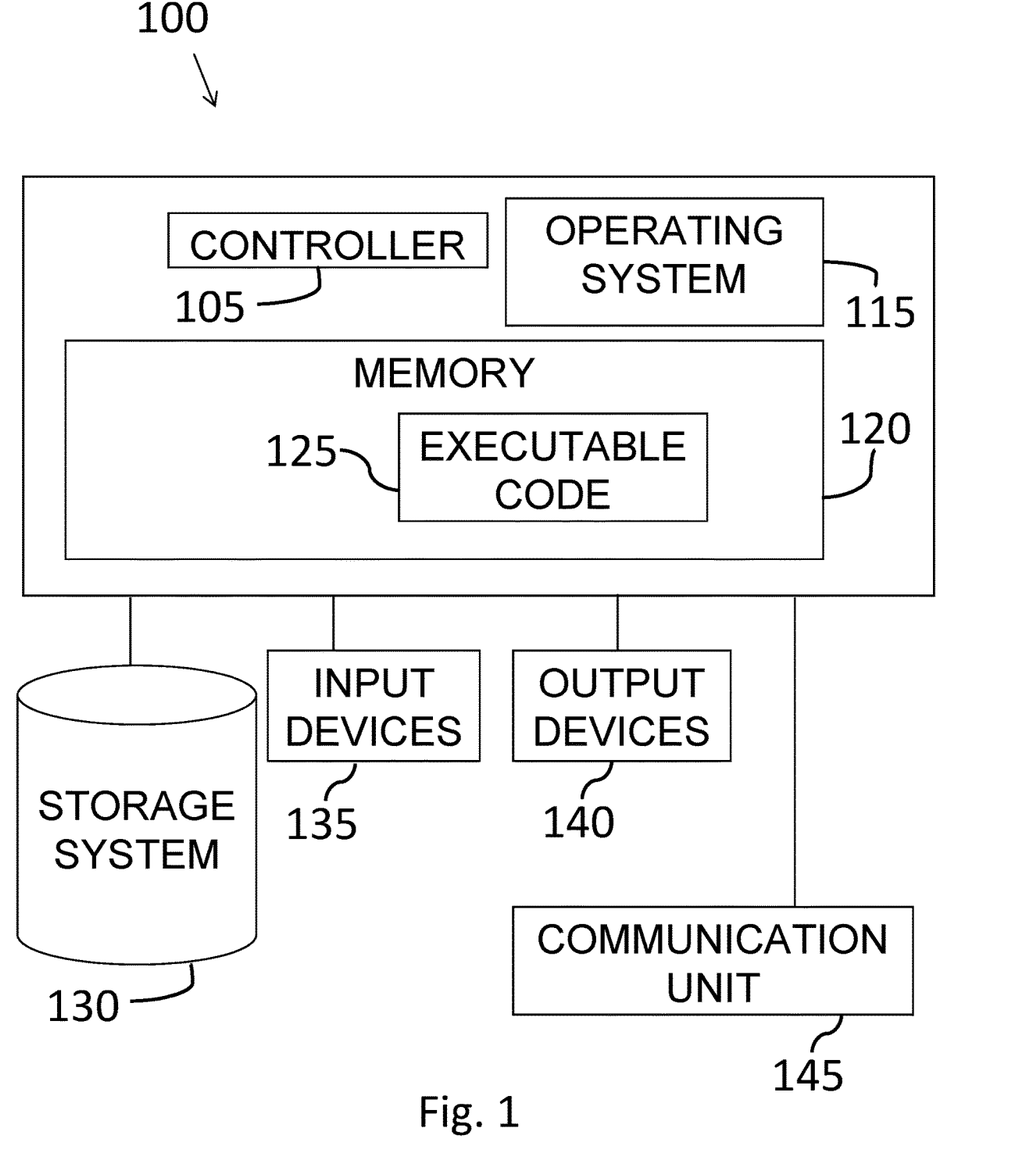
FIG. 1 shows a block diagram of a computing device, according to some embodiments of the invention.

Reference is made to FIG. 1, which is a block diagram of an example computing device, according to some embodiments of the invention. Computing device 100 may include a controller or processor 105 (e.g., a central processing unit processor (CPU), a chip or any suitable computing or computational device), an operating system 115, memory 120, executable code 125, storage 130, input devices 135 (e.g. a keyboard or touchscreen), and output devices 140 (e.g., a display), a communication unit 145 (e.g., a cellular transmitter or modem, a Wi-Fi communication unit, or the like) for communicating with remote devices via a communication network, such as, for example, the Internet. Controller 105 may be configured to execute program code to perform operations described herein. The system described herein may include one or more computing device(s) 100, for example, to act as the various devices or the components shown in FIG. 2. For example, communication system 200 may be, or may include computing device 100 or components thereof.

Operating system 115 may be or may include any code segment (e.g., one similar to executable code 125 described herein) designed and/or configured to perform tasks involving coordinating, scheduling, arbitrating, supervising, controlling or otherwise managing operation of computing device 100, for example, scheduling execution of software programs or enabling software programs or other modules or units to communicate.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of similar and/or different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be a software application that performs methods as further described herein. Although, for the sake of clarity, a single item of executable code 125 is shown in FIG. 1, a system according to embodiments of the invention may include a plurality of executable code segments similar to executable code 125 that may be stored into memory 120 and cause controller 105 to carry out methods described herein.

Storage 130 may be or may include, for example, a hard disk drive, a universal serial bus (USB) device or other suitable removable and/or fixed storage unit. In some embodiments, some of the components shown in FIG. 1 may be omitted. For example, memory 120 may be a non-volatile memory having the storage capacity of storage 130. Accordingly, although shown as a separate component, storage 130 may be embedded or included in memory 120.

Input devices 135 may be or may include a keyboard, a touch screen or pad, one or more sensors or any other or additional suitable input device. Any suitable number of input devices 135 may be operatively connected to computing device 100. Output devices 140 may include one or more displays or monitors and/or any other suitable output devices. Any suitable number of output devices 140 may be operatively connected to computing device 100. Any applicable input/output (I/O) devices may be connected to computing device 100 as shown by blocks 135 and 140. For example, a wired or wireless network interface card (NIC), a universal serial bus (USB) device or external hard drive may be included in input devices 135 and/or output devices 140.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein. For example, an article may include a storage medium such as memory 120, computer-executable instructions such as executable code 125 and a controller such as controller 105. Such a non-transitory computer readable medium may be for example a memory, a disk drive, or a USB flash memory, encoding, including or storing instructions, e.g., computer-executable instructions, which when executed by a processor or controller, carry out methods disclosed herein. The storage medium may include, but is not limited to, any type of disk including, semiconductor devices such as read-only memories (ROMs) and/or random-access memories (RAMs), flash memories, electrically erasable programmable read-only memories (EEPROMs) or any type of media suitable for storing electronic instructions, including programmable storage devices. For example, in some embodiments, memory 120 is a non-transitory machine-readable medium.

A system according to embodiments of the invention may include components such as, but not limited to, a plurality of central processing units (CPUs), a plurality of graphics processing units (GPUs), or any other suitable multi-purpose or specific processors or controllers (e.g., controllers similar to controller 105), a plurality of input units, a plurality of output units, a plurality of memory units, and a plurality of storage units. A system may additionally include other suitable hardware components and/or software components. In some embodiments, a system may include or may be, for example, a personal computer, a desktop computer, a laptop computer, a workstation, a server computer, a network device, or any other suitable computing device. For example, a system as described herein may include one or more facility computing device 100 and one or more remote server computers in active communication with one or more facility computing device 100 such as computing device 100, and in active communication with one or more portable or mobile devices such as smartphones, tablets and the like.

In some embodiments, systems and methods are provided for monitoring mental health as a mental health navigator (e.g., substantially in real time) through analysis of passively received data from personal devices (e.g., mobile devices). Digital phenotypes for different mental health conditions are created based on an iterative process of feature engineering. Predictive models for mental health conditions may be accordingly trained using artificial intelligence (AI) based algorithms.

In some embodiments, a mental behavioral profiling metric termed Mental Health Similarity Score (MHSS), is provided from analyzing passively monitored non-intrusive and non-identifiable smartphone usage data, to identify and track mental behavior. Thus, there is no need for sensors that are invasive and privacy-related such as GPS, call logs, SMS text message logs, and keyboards.

Figure 2:
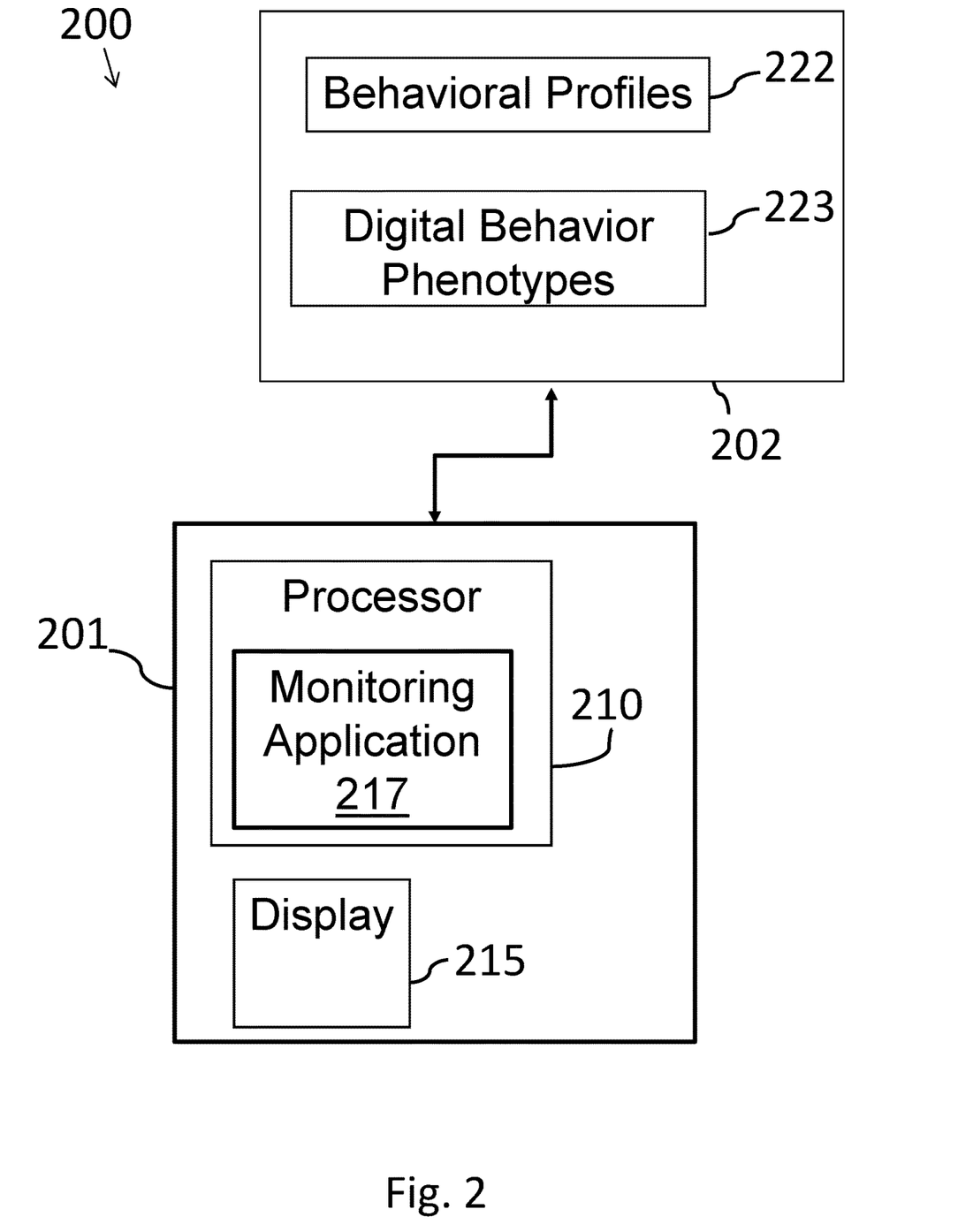
FIG. 2 shows a block diagram of a monitoring system, according to some embodiments of the invention.

Reference is now made to FIG. 2, which shows a block diagram of an assessment and monitoring system 200 for assessing and monitoring mental health of a person, according to some embodiments of the invention.

The assessment and monitoring system 200 can include a user's mobile device 201 and a server 202.

The user's mobile device 201 can include a processor 210 (e.g., such as controller 105 shown in FIG. 1), a display 215 and an assessment and monitoring application 217. The user's mobile device 201 can be a smartphone, a tablet, a smart watch, and/or any mobile device as is known in the art. The user's mobile device 201 can include one or more sensors (not shown). The user's mobile device 201 can include a proximity sensor, light sensor, accelerometer, gyrometer, or any combination thereof.

The server 202 can include a digital behavior phenotyping database 222 and a behavior profile database 223. In various embodiments, the behavior phenotyping database 222 and/or the behavior profile database 223 are stored on the user's mobile device 201.

During operation of user's mobile device 201, the assessment and monitoring application 217 can be activated by a user. The user can activate the assessment and monitoring application 217 by downloading the application, e.g., via App Store® on an iPhone® or Google Play® on an Android® phone, and opening the application for it to begin.

Once the assessment and monitoring application 217 is activated by a user it can continually run in the background, recording digital activity data of the user. The digital activity data can be recorded into a dedicated memory location on the user's mobile device for a predetermined duration (e.g., 30 minutes, 1 hour, 2 hours, 3 hours, 24 hours). Once the predetermined duration is reached, the digital activity data can be transmitted to the server 202. The predetermined duration can be specified by a user in the activation of the assessment and monitoring application 217, specified as a coded parameter in the application, or any combination thereof.

In some embodiments, the predetermined duration is modified in real-time depending upon the user's mental health condition. For example, assume at the beginning of the assessment and monitoring application 217 the user is monitored every 4 hours and the mental health is similar, then the assessment and monitoring application 217 can automatically update the predetermined duration to extend the duration by an interval (e.g., 1 hour) until there is an interval where some change in mental health condition is detected or a maximum duration is met (e.g., 24 hours). Assume in the same example, instead of the user's mental health condition being the same every 4 hours, it is divergent beyond a tolerance threshold, then the assessment and monitoring application 217 can automatically update the predetermined duration to reduce the duration by an interval (e.g., 45 minutes) until there is an interval where some stable mental health condition is detected or a minimum duration is met (e.g., 15 minutes).

The assessment and monitoring application 217 can be closed by a user or can close after a predetermined duration (e.g., 1 month, 2 months, 6 months).

The assessment and monitoring application 217 can monitor the digital activity data. The digital activity data that is monitored can include application usage parameters for other applications that the user engages with on the mobile device. The application usage parameters can include name of mobile application, time of opening the mobile application, time of closing the mobile application, time duration of inactivity when the mobile application is not used, type of the mobile application, or any combination thereof.

The digital active data can refrain from including personal content of the user (e.g., user name, precise location, without tapping into searches or input text or capturing any images IP address, and/or any other information that can be used to identify the user). In this manner it can be possible to protect an identify of the user. This can be important when assessing and monitoring the mental condition of a user, as many users can be apprehensive about personally identifying information of their mental condition being recorded and transmitted over the internet.

In some embodiments, the monitored applications are classified into categories based on categorization such as social, communication, gaming, and tools.

The digital activity data can be transmitted from the user's mobile device 201 to the server 202.

The server 202 can receive the digital activity data. The behavior profiles 222 can include a behavior profile model for each mental condition (e.g., depression, attention deficit disorder, bi-polar, emotional burn-out, or any mental condition). The behavior profiles 222 can be machine learned models. The machine learned models can be machine learned models as determined via neural network (NN).

The neural network (NN) can refer to an information processing paradigm that may include nodes, referred to as neurons, organized into layers, with links between the neurons. The links can transfer signals between neurons and can be associated with weights. A NN may be configured or trained for a specific task, e.g., pattern recognition or classification. Training a NN for the specific task may involve adjusting the weights based on examples. Each neuron of an intermediate or last layer may receive an input signal, e.g., a weighted sum of output signals from other neurons, and may process the input signal using a linear or nonlinear function (e.g., an activation function). The results of the input and intermediate layers may be transferred to other neurons and the results of the output layer may be provided as the output of the NN. Typically, the neurons and links within a NN are represented by mathematical constructs, such as activation functions and matrices of data elements and weights. A processor, e.g., CPUs or graphics processing units (GPUs), or a dedicated hardware device may perform the relevant calculations.

The behavior models can be training via the NN as unsupervised, with un-biased clustering of the behavioral profiles 222 (e.g., updated with features that are used for clustering). The clustering algorithms may attempt to group the users based on predetermined features. The predetermined features may include at least one of: session time of the application, frequency of application use, gap between using applications, longest gap in a day (or digital sleep time), and type of digital interaction (active vs. passive) identified based on use of keyboard, time patterns of digital interaction (per second, hour, day, week, month, or year) quantified through measures such as entropy, regularity index, etc. The applications may be further classified based on their category for grouping.

The training of the behavior profile models be carried out with supervised training of predictive models using an ensemble of AI-algorithms (e.g., updated with specific algorithms that have been used for specific mental health conditions) that are optimized for various mental health indications. For example, ML models may be built using Random Forest, K-Nearest Neighbor, XGD-Boost, and Support Vector Machine (SVM).

In some embodiments, the behavior profile models may undergo supervised training for behavior of known mental health conditions, based on the clustered behavioral profiles from the unsupervised training. The supervised training of the behavior profile models may be used to learn non-linear relationships between the time users spend on their devices and the types of applications they are using as a function of their mental health.

In some embodiments, the behavior profile models may have continuous updates of models through re-enforcement learning from user feedback. For example, a user can rate an output of the mental health condition, and that rating can be used to further train the models. In some embodiments, a Markov Decision Process can be used.

In order to correct for any bias due to inaccurate self-reporting of a user's mental health condition and the subjective, clinical experience-based nature of mental health diagnosis administered today, unsupervised learning via k-means clustering can be used to learn hidden sub-diagnosis clusters. As each mental health condition may be regarded as a spectrum, k-means clustering enables the behavior profile models to find the subtle differences between sub-groups thus binning users into a deeper, more personalized category of their mental health condition.

In various embodiments, three machine learning techniques are used in order to characterize mental health patterns of users of the system. By collecting whether or not the user has been diagnosed with a mental health condition, for instance as the user logs in to the system 200, labels of classification can be created for the supervised training methods.

In some embodiments, sensor data of the user's device can be used as an input to train the behavior profile models. The sensor data can include data from a proximity sensor, light sensor, gyrometer, and/or accelerometer. The sensor data can be an indicator of anticipated dopamine levels for a user.

The behavior profile models can be trained with large datasets (e.g., 3 months of daily digital interactions and sensor data captured using the assessment and monitoring application 217 and transmitted periodically to the server 202) of data captured from many users (e.g., general users wanting to understanding their mental status, specific cohorts such as the US Veterans, population from specific demographic or ethnic origin, individuals with certain pre-diagnosed mental health condition(s)).

During updated training of the behavior profile models based on digital activity data received from the mobile device, unsupervised clustering may be applied for clinical research and/or evaluation. In case of no clinical significance, a new feature may be trained. Supervised training may be carried out based on clinical ground truth (e.g., with known mental health conditions) as well as the results of the clustering, until a digital phenotype model may be achieved.

Features extracted from the digital activity serve as a representation of the behavior profile 222 that can be compared with the pre-trained digital behavior phenotypes 223 (e.g. ML models for different mental behavioral profiles). For each mental health condition that there is a digital behavior phenotype 223, the digital behavioral profile 222 derived from the digital activity data can be compared against a corresponding digital behavior phenotype 223 for similarity. For example, a depression similarity score can be determined by comparing a day's digital activity data with the digital behavior phenotype for depression. If they are sufficiently similar, then the user may be classified to have a behavioral profile with someone who has depression. As is apparent to one of ordinary skill, this comparison can be done for each mental health condition. Thus, the mental health similarity score (MHSS) is the probability percentage computed as the likelihood of match between a pre-trained digital phenotype model and the digital behavioral profile.

The similarity score (e.g., a percentage similarity) can be reported number between 1 and 100. Where 100 refers to perfect match to someone with that specific mental behavioral profile, and 1 refers to very poor or no match at all.

The similarity score can be displayed to a user via the display on the user's mobile device. In some embodiments, the similarity score is a confidence level for a match to someone with that specific mental behavioral profile.

In various embodiments, the user's mobile device 201 in the assessment and monitoring system 200 is replaced with a desktop system, a gaming system, a set top box, a watch, a virtual assistant technology, or any computing device that a user can run applications on. In these various embodiments, the assessment and monitoring application 217 can be downloaded onto these various platforms such that the assessment and monitoring of the digital activity data as described above can be performed on these various platforms.

In some embodiments, a baseline behavior may be created for the user, where the baseline is determined by the digital activity data for the user over a predefined time period (e.g., 2 weeks). In case that subsequent monitored data deviates from the baseline by a predefined threshold, an alert may be issued (e.g., by the processor 201) to the user, e.g., via the display.

In various embodiments, the user can monitor their mental condition daily. In some embodiments, the user can monitor their mental condition over a time period by requesting the application keep track for a predetermined time period. In this manner, the user who was initially provided a health condition of depression may choose to not interact with the system at all, take actions to treat the depression and then after a predetermined time period see the similarity score to depression every day. This way the user may see what improves their depression or when the depression is getting worse.

In another example, a new user uses the system 200 without prior diagnosis (e.g., a veterans family urges him to use a mental health monitoring service for suspected depression). The user may get a similarity score of 94% for depression and 86% for anxiety. In case of a similarity scores that deviates from a baseline by a predefined threshold (e.g., over 80%), the user may receive a notification encouraging them to seek consultation for mental health issues, while the system 200 may provide monitoring of digital behavior and its influence on the similarity score.

For example, training the ML model using random forest, the calculated days for the condition of depression is 1734, while the actual number of depression days is 2974. In another example, training the ML model using random forest the calculated days for the condition of anxiety is 1533, while the actual number of depression days is 2774. In another example, training the ML model using random forest the calculated days for the condition of ADHD is 1003, while the actual number of depression days is 1805.

For example, training the ML model using KNN model, the calculated days for the condition of depression is 2244, while the actual number of depression days is 2974. In another example, training the ML model using random forest the calculated days for the condition of anxiety is 1928, while the actual number of depression days is 2774. In another example, training the ML model using random forest the calculated days for the condition of ADHD is 1485, while the actual number of depression days is 1805.

Figure 3A:
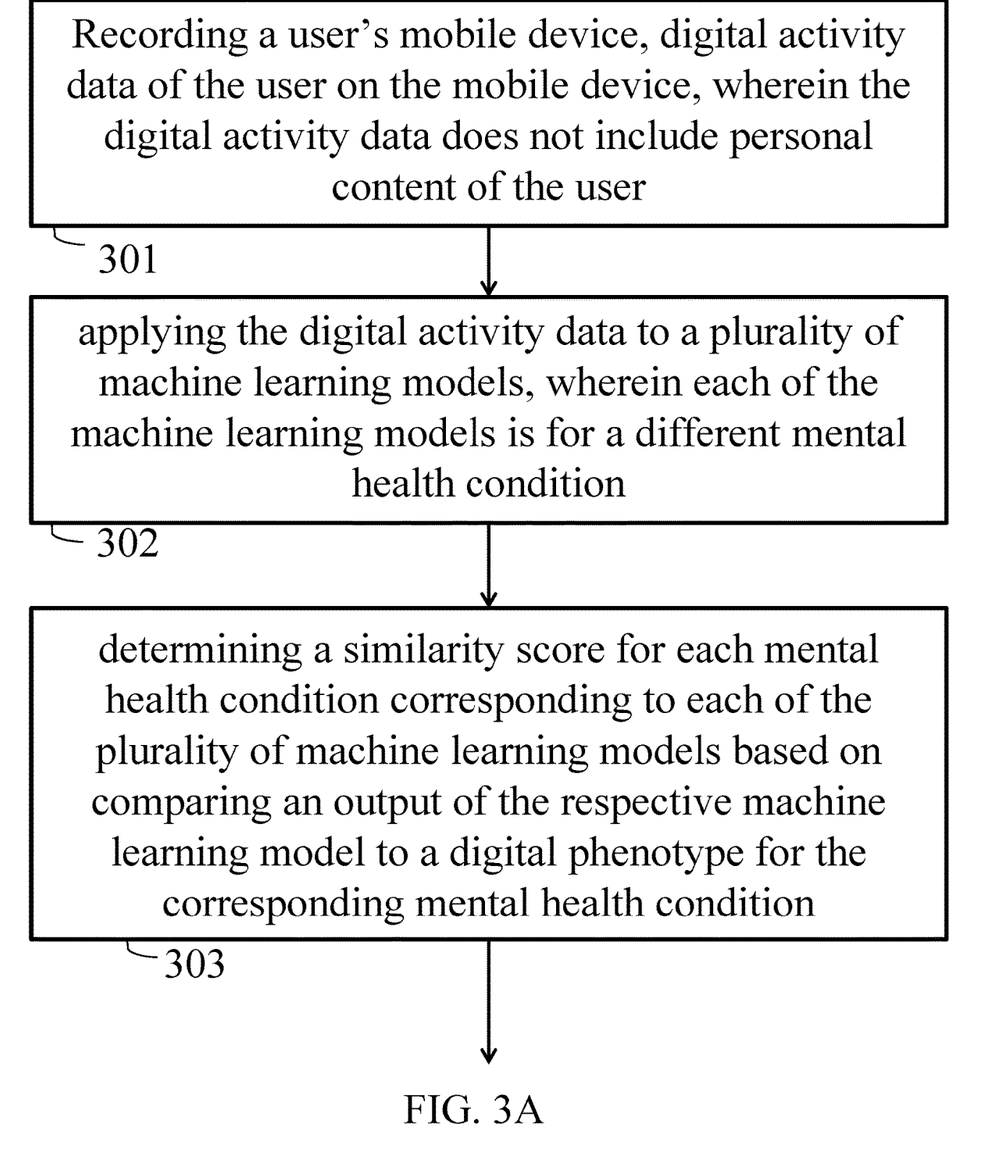
FIGS. 3A and 3B show a flowchart of a method for assessing and monitoring a mental health condition, according to some embodiments of the invention.
Figure 3B:
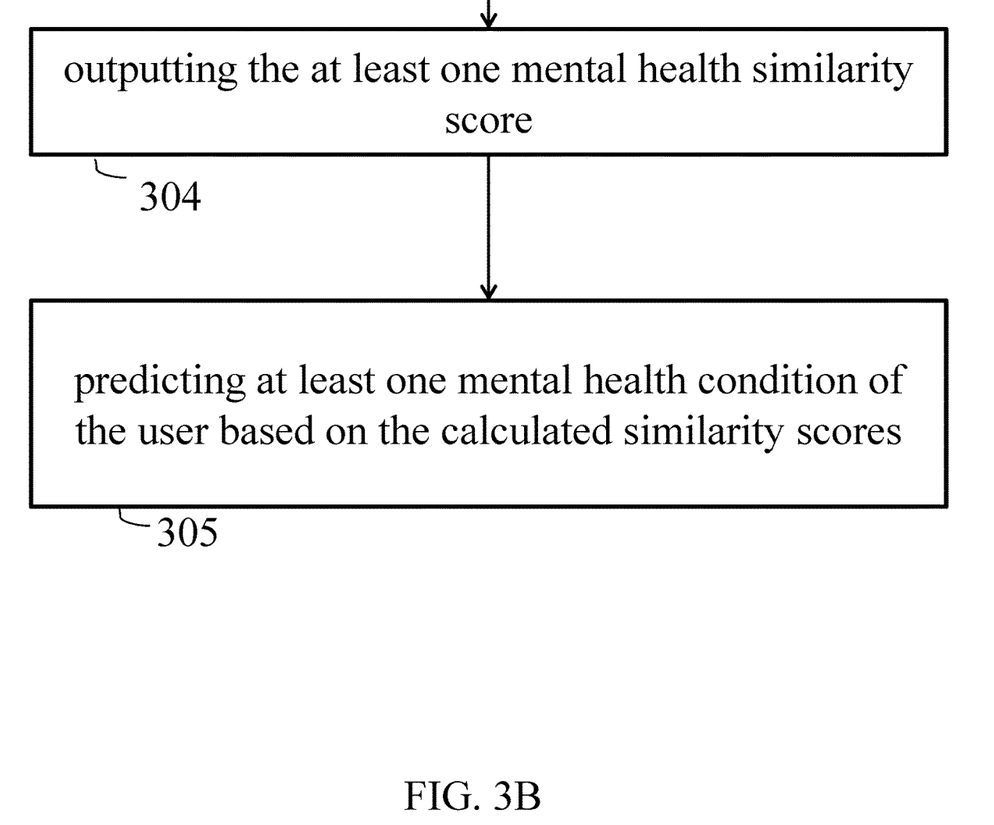

Reference is now made to FIGS. 3A-3B, which show a flowchart for assessing mental health of a person, according to some embodiments of the invention.

The method involves recording digital activity data of the user on a mobile device (e.g., mobile device 201 as described above in FIG. 2) wherein the digital activity data does not include personal content of the user (Step 301). As described above in FIG. 2, the recording can be performed by an application that runs in the background of the user's mobile device.

The method can also involve applying the digital activity data to a plurality of machine learning models (e.g., behavior profiles 222 as described above in FIG. 2), wherein each of the machine learning models is for a different mental health condition (Step 302). The mental health conditions can include depression, anxiety, attention deficit disorder, post-traumatic stress disorder, bi-polar disorder and/or any condition as is known in the art.

The method can also involve determining a similarity score for each mental health condition corresponding to each of the plurality of machine learning models based on comparing an output of the respective machine learning model to a digital phenotype for the corresponding mental health condition (Step 303). The similarity score can be determined as described above in FIG. 2.

The method can also involve outputting, at a display of the user's device, or any other user authorized system, the at least one mental health similarity score (Step 304). The user authorized system can be any assisting system for the user, such as a personal computer or a computing device of a medical professional, such that the similarity score is displayed on a user's display. The method can also involve predicting at least one mental health condition of the user based on the calculated similarity scores (Step 305), for instance using a dedicated AI-algorithm.

In some embodiments, the mental health similarity score that is associated with one or more conditions is displayed (at a display of the user's device, or any other user authorized system). The decision of a mental health disorder can accordingly be based on the similarity score monitored over a period of time typically. Thus, the user can receive only a similarity score corresponding to one or many mental health conditions, without specific indication of a mental health condition.

In some embodiments, the digital activity data of the user can be used to further train the behavior profile models. In this manner, the behavior profile models can be trained without using personal information, thus there can be a lack of subjectivity in model training. This can allow for a more accurate diagnoses due to an unbiased model creation that is not impacted by subjective user input.

In an example case, active and passive data was collected in a longitudinal observational sampling using a dedicated mobile app, derived from a cohort of 558 participants over the age of 18. Of the 469 individuals who reported having no diagnosis as their current status in their demographics questionnaire, 307 (65.5%) scored as moderate to severe depression (with PHQ-9 score ≥10).

The dedicated mobile app in this example is a mental health screening application that passively collects personal device use data with zero respondent burden and no use of identifiable information. The dedicated mobile app can require connectivity to send data to the back end for analysis and receive data analysis outcomes, while not requiring connectivity to collect the data. The dedicated mobile app works as an always-on solution, where individuals can register or log in to the app with no supervision, and any required onboarding information was easily made available to the participants remotely. In addition, demographic user profile information questions (gender, age, and existing mental health indication) can be answered within the app.

The dedicated mobile app can use the principle of digital phenotyping to track user behavior. It displays an MHSS score developed from phone use metrics such as time spent on various apps on a daily and weekly basis. The MHSS displays how similar the user's digital behavior is to the digital behavior of someone who has been diagnosed with depression.

Depression severity can be assessed using a patient-reported outcome measurement questionnaire. The participants answered the PHQ-9 using the dedicated the app. The PHQ-9 scale is the current standard method for detecting and measuring the severity of depression worldwide. The PHQ-9 measures depression severity over the preceding 2 weeks. Each item of the PHQ-9 is scored on a scale of 0 (not at all) to 3 (nearly every day). The total PHQ-9 score ranges from 0 to 27, with a score of ≥10 indicating a major depressive disorder. A score of <5 indicates no depression, 5 to 9 indicates mild depression, 10 to 14 indicates moderate depression, 15 to 19 indicates moderately severe depression, and 20 to 27 indicates severe depression.

The distribution of the PHQ-9 scores was as follows: 11.3% (63/558) were in the none category (e.g., they were not depressed) with PHQ-9 scores <5, whereas 88.7% (495/558) showed signs of depression by scoring between mild and severe. The mean PHQ-9 score was 12.5 (SD 6.29). Out of the 558 participants, 499 (89%) answered "no previous diagnosis" in the demographic questions collected at onboarding. Moreover, 65% (323/499) of the participants who reported that they had no previous diagnosis of any kind obtained a PHQ-9 score of at least moderate (≥10) to severe depression.

Digital biomarkers, used as machine learning features in this example, were calculated per user, taking daily behavioral patterns on a 24-hour basis starting from midnight every day. The 3 main types of non-sensor features were average time on the phone per day, frequency of events per day, and app category use per day.

A mental health profiling metric termed MHSS can be derived from the features extracted from the raw data to classify whether a user's daily digital behavior mimicked the digital behavior of mobile users who are depressed. This metric is a direct output of a machine learning model trained to classify 24 hours of digital behavior into the different thresholds of the PHQ-9, screening positive for severe depression versus no depression. A variety of machine learning models were compared to detect major digital behavioral differences between none and severe category participants. The algorithms include random forest regression, multivariate adaptive regression splines, random forest classification, extreme gradient boosting, and support vector machines with a radial basis function kernel. After the top algorithm was chosen based on the highest predictive accuracy, 4 machine learning models were created and compared: the PHQ-9 binary non-sensor model, the PHQ-9 binary gyroscope sensor model, the PHQ-9 3-class model, and the PHQ-9 question-specific models. Finally, a model can be built using specific PHQ-9 items that had the highest correlations with the non-sensor passive digital biomarkers to detect specific symptoms of depression rather than classifying them into none and severe categories.

Among the classification algorithms, random forest proved to have the highest predictive accuracy (87%). Extreme gradient boosting followed with an accuracy of 86%, whereas the support vector machine classifier had the lowest accuracy (44%). The top-performing algorithm, the random forest classifier trained on the PHQ-9 binary non-sensor model (none vs severe on the depression rating scale) on 34 of the nonsensor features, achieved a precision of 85% to 89%, recall of 85% to 89%, F1 of 87%, and overall accuracy of 87%. In addition, the model was tested to see whether it could accurately predict participants who had reported a previous diagnosis of depression. The model achieved an accuracy of 80% in detecting depression but only 26% in detecting the none group. When the gyroscope features were added as additional markers, the overall accuracy dropped to 76% with a precision of 74% to 78%, recall of 67% to 83%, and F1 of 72% to 78%. This model was also tested on the self-proclaimed diagnosis cohort and achieved 27% accuracy in detecting depression and 0% accuracy in detecting the none group. When age and gender were added to see if demographics played a role in classifying none (not depressed) versus severe (depressed) cohort participants, the overall accuracy decreased slightly from 87% to 84%, precision increased from 82% to 87%, recall increased from 83% to 86%, and F1 increased from 84% to 85%.

The MHSS models reached an overall accuracy of 87% with an average of 10 days of smartphone data were used in addition to PHQ-9 results from 399 participants to demonstrate the ability to detect digital behavioral markers quantified from the participants' smartphones to detect depression severity. We further focused on using these digital behavioral markers to develop predictive models to classify none (not depressed) and severe (depressed) symptom severity scores. Thus, although gyroscope sensor data show some distinction between the 2 cohorts when including them as an additional feature, the gyroscope as a sensor alone does not add predictive power.

While certain features of the invention have been illustrated and described herein, many modifications, substitutions, changes, and equivalents may occur to those skilled in the art. It is, therefore, to be understood that the appended claims are intended to cover all such modifications and changes.

Various embodiments have been presented. Each of these embodiments may of course include features from other embodiments presented, and embodiments not specifically described may include various features described herein.

The invention claimed is:

1. A computer implemented method for assessing mental health of a person, the method comprising:
   recording, by a processor of a user's mobile device, digital activity data of the user on the mobile device for a predetermined duration, wherein the digital activity data does not include personal content of the user;
   applying, by the processor of the user's mobile device, the digital activity data to a plurality of machine learning models, wherein each of the machine learning models represents a digital phenotype for a different mental health condition;
   determining one or more behavioral profiles to train the machine learning models, wherein the behavioral profiles are clustered based on digital phenotypes indicative of at least one mental health condition;
   determining, by the processor of the user's mobile device, a similarity score for each mental health condition corresponding to each of the plurality of machine learning models based on comparing an output of the respective machine learning model to a digital phenotype for the corresponding mental health condition, wherein the similarity score is a confidence level for a match to someone with that specific mental health condition;
   outputting, at a user's display, the at least one mental health similarity score; and
   predicting, by the processor, at least one mental health condition of the user based on the calculated similarity scores,
   wherein the predetermined duration is modified in real-time depending upon the at least one mental health condition.

2. The method of claim 1, wherein the recording is performed by an application that runs in the background of the user's mobile device.

3. The method of claim 1, comprising:
   creating a baseline state for the user, wherein the baseline state is determined by the at least one mental health condition for a predefined time period; and
   issuing an alert, if the at least one mental health condition deviates from the baseline state by a predefined threshold.

4. The method of claim 1, further comprising using the digital activity data to further train the plurality of machine learning models.

5. The method of claim 1, wherein the received digital activity data is used to extract features associated with information selected from the group consisting of: time of usage of the mobile device, type of program running on the mobile device, and frequency of using the same program running on the mobile device.

6. The method of claim 1, comprising applying a model using machine learning algorithms based on autonomous clustering of behavioral profiles, wherein the training is unsupervised.

7. The method of claim 1, wherein the machine learning model is trained using algorithms selected from the group consisting of: Linear Regression, Random Forest, K-Nearest Neighbor, XGD-Boost, and Support Vector Machine (SVM), wherein the training is supervised given user input as pre-labelled data.

8. The method of claim 1, comprising performing reinforcement learning on the machine learning models based on a feedback loop, using a Markov Decision Process.

9. A system for assessing mental health of a person, the system comprising:
   a server; and
   a processor of a user's mobile device, wherein the processor is in communication with the server, and wherein the processor is configured to:
      record digital activity data of the user on the mobile device for a predetermined duration, wherein the digital activity data does not include personal content of the user; and
      send the recorded digital activity data to the server;
   wherein the server is configured to:
      apply the digital activity data to a plurality of machine learning models, wherein each of the machine learning models represents a digital phenotype for a different mental health condition;
      determine one or more behavioral profiles to train the machine learning models, wherein the behavioral profiles are clustered based on digital phenotypes indicative of at least one mental health condition;
      determine a similarity score for each mental health condition corresponding to each of the plurality of machine learning models based on comparing an output of the respective machine learning model to a digital phenotype for the corresponding mental health condition wherein the similarity score is a confidence level for a match to someone with that specific mental health condition; and
      send at least one mental health similarity score for displaying on a user's display; and
      predict at least one mental health condition of the user based on the calculated similarity scores,
      wherein the predetermined duration is modified in real-time depending upon the at least one mental health condition.

10. The system of claim 9, wherein the recording is performed by an application that runs in the background of the user's mobile device.

11. The system of claim 9, wherein the server is configured to:
    create a baseline state for the user, wherein the baseline state is determined by the at least one mental health condition for a predefined time period; and
    issue an alert, if the at least one mental health condition deviates from the baseline state by a predefined threshold.

12. The system of claim 9, wherein the digital activity data is used to further train the plurality of machine learning models.

13. The system of claim 9, wherein the received digital activity data is used to extract features associated with information selected from the group consisting of: time of usage of the mobile device, type of program running on the mobile device, and frequency of using the same program running on the mobile device.

14. The method of claim 13, wherein the server is configured to perform machine learning algorithm based on autonomous clustering of behavioral profiles, wherein the algorithm is unsupervised.

15. The method of claim 13, wherein the machine learning model is trained using algorithms selected from the group consisting of: Linear Regression, Random Forest, K-Nearest Neighbor, XGD-Boost, and Support Vector Machine (SVM), wherein the training is supervised given user input as pre-labelled data.

16. The method of claim 13, wherein reinforcement learning is performed on the machine learning models based on a feedback loop, using a Markov Decision Process.

\* \* \* \* \*